(12) United States Patent
Saccomanno (10) Patent No.: US 7,498,004 B2
(45) Date of Patent: Mar. 3, 2009

(54) ULTRAVIOLET DISINFECTING APPARATUS

(75) Inventor: Robert J. Saccomanno, Montville, NJ (US)

(73) Assignee: Honeywell International Inc., Morristown, NJ (US)

( * ) Notice: Subject to any disclaimer, the term of this patent is extended or adjusted under 35 U.S.C. 154(b) by 1249 days.

(21) Appl. No.: 10/284,709

(22) Filed: Oct. 30, 2002

(65) Prior Publication Data
US 2003/0086848 A1 May 8, 2003

Related U.S. Application Data

(63) Continuation-in-part of application No. 10/268,567, filed on Oct. 9, 2002, now Pat. No. 6,773,584.

(60) Provisional application No. 60/336,381, filed on Nov. 2, 2001.

(51) Int. Cl.
*A61L 9/00* (2006.01)
*A61L 2/00* (2006.01)
*A62B 7/08* (2006.01)
*B01J 19/08* (2006.01)
*G01N 21/00* (2006.01)
*G01N 23/00* (2006.01)
*B03C 3/38* (2006.01)

(52) U.S. Cl. ............... 422/306; 422/1; 422/4; 422/5; 422/24; 422/121; 422/186; 422/186.3; 422/292; 422/900; 250/453.11; 250/454.11; 250/455.11; 96/16; 96/223; 96/224; 96/FOR. 175

(58) Field of Classification Search ............ 422/1, 422/4–5, 24, 121, 186, 186.3, 292, 306, 900; 250/453.11, 454.11, 455.11; 96/16, 223, 96/224, FOR. 175
See application file for complete search history.

(56) References Cited

U.S. PATENT DOCUMENTS

| | | | |
|---|---|---|---|
| 3,170,980 A | | 2/1965 | Pritchard |
| 3,744,216 A | | 7/1973 | Holloran |
| 4,255,383 A | * | 3/1981 | Schenck ............... 422/24 |
| 4,260,220 A | | 4/1981 | Whitehead |
| 4,633,079 A | * | 12/1986 | Rieger ............... 250/227.14 |
| 5,034,235 A | * | 7/1991 | Dunn et al. ............ 426/238 |
| 5,573,730 A | * | 11/1996 | Gillum ............... 422/123 |
| 5,625,738 A | | 4/1997 | Magarill |
| 5,721,795 A | * | 2/1998 | Pelka ............... 385/37 |
| 5,742,063 A | * | 4/1998 | Scroggins et al. ...... 250/455.11 |
| 6,160,948 A | * | 12/2000 | McGaffigan ............ 385/146 |
| 6,228,327 B1 | | 5/2001 | Matschke |
| 6,391,259 B1 | * | 5/2002 | Malkin et al. ............ 422/28 |
| 6,447,720 B1 | * | 9/2002 | Horton et al. ............ 422/24 |
| 6,656,424 B1 | * | 12/2003 | Deal ............... 422/3 |

FOREIGN PATENT DOCUMENTS

| | | |
|---|---|---|
| EP | 0 461 310 | 12/1991 |
| JP | 04 033659 | 5/1992 |

* cited by examiner

*Primary Examiner*—Jill Warden
*Assistant Examiner*—Monzer R Chorbaji
(74) *Attorney, Agent, or Firm*—Oral Caglar, Esq.

(57) ABSTRACT

Ultraviolet radiation is used to disinfect air (105) in a flow tube (110), where the flow tube (110) includes total internal reflecting features (120) on a portion of its external surface and said ultraviolet radiation propagates through a portion of the flow tube via total internal reflection.

20 Claims, 6 Drawing Sheets

ULTRAVIOLET DISINFECTING APPARATUS

RELATED APPLICATIONS

This application is a continuation-in-part of the U.S. patent application Ser. No. 10/268,567, filed Oct. 9, 2002, now U.S. Pat. No. 6,773,584, Aug. 10, 2004, and relies on the disclosure of U.S. Provisional Patent Application Ser. No. 60/336,381, filed Nov. 2, 2001, both of which are incorporated herein by reference.

BACKGROUND OF THE INVENTION

1. Technical Field

This invention relates to an air purification system using intense ultraviolet irradiation to break down chemical bonds in toxic compounds and to de-activate pathogens. The method can also be applied to any mass transport, including the purification of water or other fluids containing naturally occurring toxins or those resulting from biological and chemical agents used in warfare.

2. Background Art

Prior art UV disinfecting systems are typically water disinfecting systems where the water is exposed to UV radiation such that the radiation passes through the water, strikes a reflecting surface and then again passes through the water after reflection. The reflecting surfaces, typically polished stainless steel, absorb a significant amount of radiation. Air disinfection systems, such as that described by Halloran (U.S. Pat. No. 3,744,216) employ extended-arc low pressure mercury germicidal lamps within an airstream. Companies such as American Ultraviolet and Steril-Aire manufacture systems that use these lamps within duct of a heating, ventilating, and air conditioning (HVAC) system, providing germicidal action.

In Whitehead, U.S. Pat. No. 4,260,220, a square cross-section hollow tube waveguide is constructed, operating under the principle of total internal reflection (TIR). Each wall section has a planar inner surface and an outer surface having 90° angle longitudinal corrugations. The walls are constructed of transparent dielectric material, such as acrylic or optically clear glass. The Whitehead device is used to transport visible light.

A square cross section light waveguide is known in the art to maximum flux homogeneity in a short distance according to Pritchard (U.S. Pat. No. 3,170,980). These devices are typically employed in projection systems between a the light source and an imaging device such as for example is described in Magarill (U.S. Pat. No. 5,625,738).

Common to the prior art UV disinfection systems is over-dosage of ultraviolet (UV) radiation to the air being disinfected, which necessarily increases the size, weight, and power of the resulting equipment. There is a long-felt need to improve the efficiency of such systems and also to provide a portable efficient UV disinfecting system for air.

SUMMARY OF THE INVENTION

My invention is an apparatus and method for disinfecting air that channels air through one end of a hollow totally internally reflecting light conduit or waveguide and couples ultraviolet (UV) energy from a high intensity lamp through the conduit or waveguide from the other end. The waveguide itself is constructed of a non-UV-absorbing material, such as UV-grade fused silica glass. Advantageously, the use of light-pipe technology, which is based on total internal reflection (TIR), ensures that all the input UV radiation is dissipated in the air.

DESCRIPTION OF THE INVENTION

Mode(s) for Carrying Out the Invention

Figure 1:
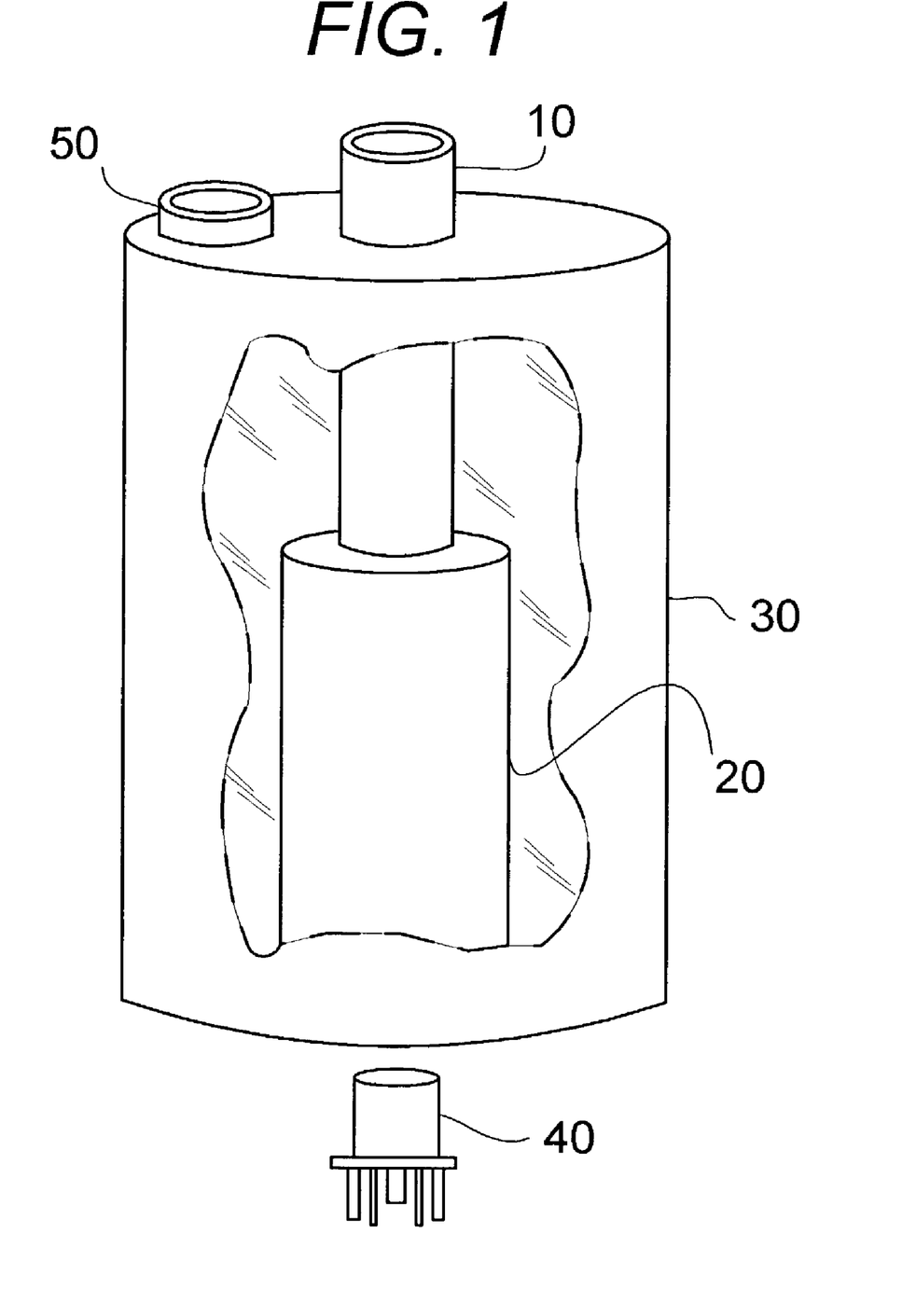
FIG. 1 depicts an apparatus for disinfecting water using ultraviolet radiation (UV) in accordance with one illustrative embodiment of my invention.

Referring first to FIG. 1, the basic construction of an ultraviolet (UV) water disinfecting device in accordance with my invention is shown, including a fluid inlet tube 10 that acts as a central light pipe, an optical cladding tube 20 around the lower portion of fluid inlet tube 10 and defining therewith a concentric gap 15, a fluid containment vessel 30, a fluid outlet tube 50, and a high intensity UV lamp 40, such as a flashlamp.

Figure 2:
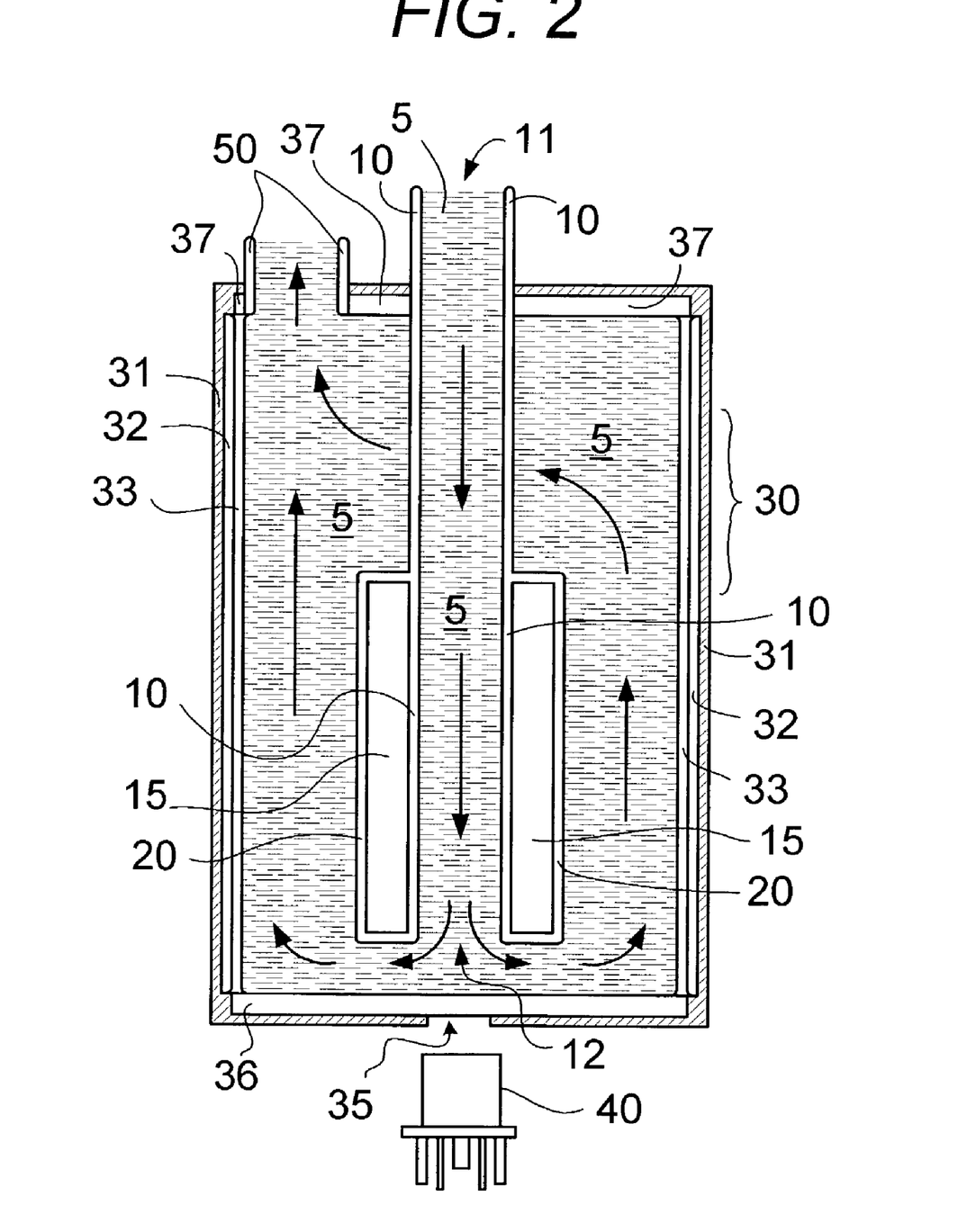
FIG. 2 depicts a sectional view of the UV disinfecting apparatus of FIG. 1.

Referring next to FIG. 2, the fluid containment vessel 30 includes an internal surface configured as an ultraviolet mirror 31; for example, the fluid containment vessel may be constructed from aluminum and the internal surface may be polished aluminum. A fluid 5 to be disinfected, such as water, enters the fluid inlet tube 10 through an entrance end 11. The fluid inlet tube 10 may be manufactured, for example from UV-grade fused silica.

The fluid 5 travels through the fluid inlet tube 10 towards the high intensity UV lamp 40 and exits the fluid inlet tube 10 at the exit end 12. The fluid 5 flow then is redirected by an ultraviolet (UV) transmissive window lower surface 36, which forms a portion of the lower end of fluid containment vessel 30. Next, the fluid 5 flow is redirected to the fluid outlet tube 50, which is located in the upper end of the fluid containment vessel 30.

The fluid 5 is contained within the fluid containment vessel 30. The fluid containment vessel 30 includes an inner tube 33, which may be constructed from UV-grade fused silica, contained within an outer aluminum shell with a reflective interior surface defining a UV mirror 31, with a gap 32, such as an air gap, between the outer shell and the inner tube 33. Then ends of the outer tube 30 are closed off with the lower ultraviolet window surface 36 and an ultraviolet window upper surface 37.

The preferred orientation of the ultraviolet (UV) water disinfecting device is vertical, so that the fluid 5 flow approximates plug-flow, and the position of the fluid outlet tube 50 is at or near the highest point, allowing for quick and efficient removal of undesirable air bubbles. Air bubbles present in the fluid 5 can form scattering sites for the UV radiation thereby degrading system efficiency. These UV scattering sites result in UV radiation being directed at less than optimum angles causing reflections from the fluid containment vessel internal surface, the ultraviolet mirror 31 that is approximately 86% reflective when composed of aluminum tube. Without these UV scattering sites, the ultraviolet radiation is dissipated mostly within the fluid 5, because all reflections are near loss-less because of the total internal reflection (TIR) operation of a light pipe.

Figure 3:
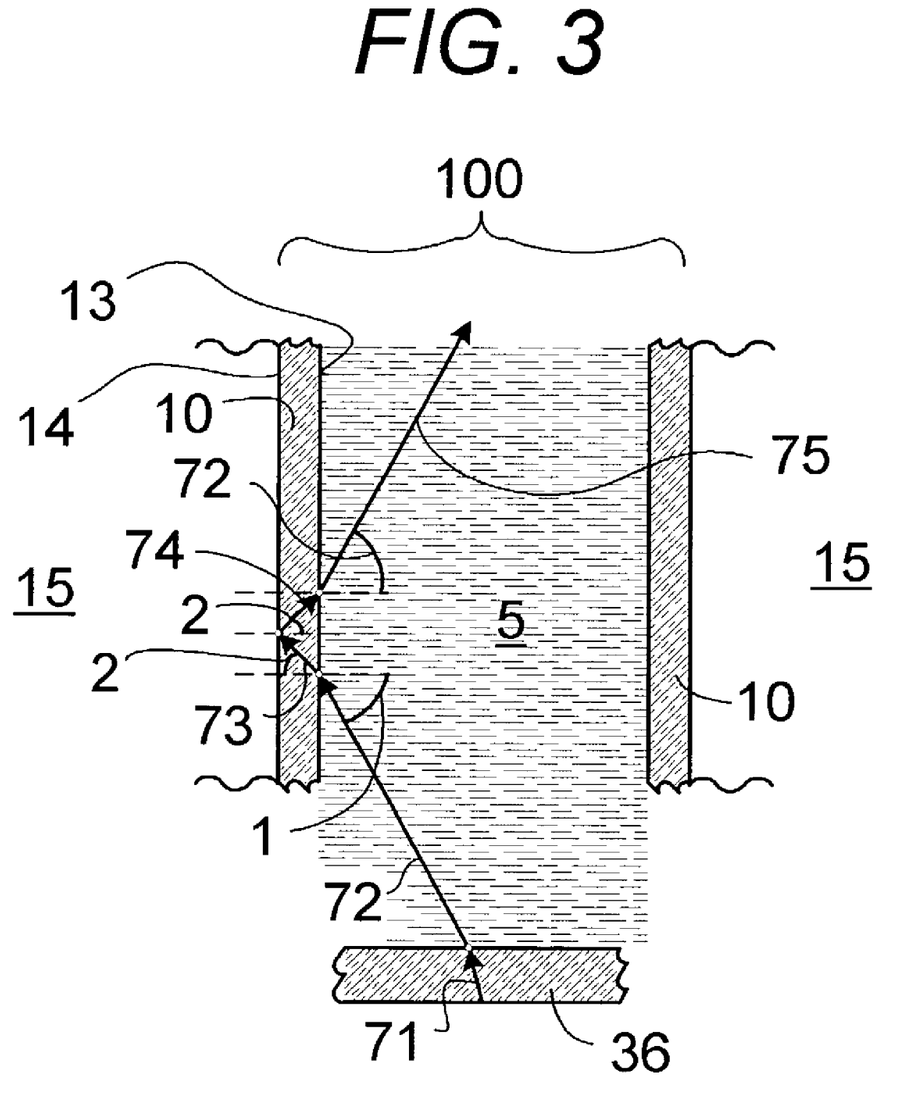
FIG. 3 depicts a light pipe irradiation zone within the UV disinfecting apparatus of FIG. 1, showing how the ultraviolet radiation is contained using total internal reflection (TIR).

Referring next to FIG. 3, a light pipe 100 region is formed from the fluid 5, such as water, the fluid inlet tube 10, such as a UV-grade fused silica tube, and the concentric gap 15, such as an air gap or a vacuum gap. The concentric gap 15 is hydraulically isolated from the fluid 5, in order to allow the light pipe 100 to operate. Light pipe operation is based on the refractive index of the concentric gap being less than the refractive index of the fluid 5. The refractive indices of fused silica and water in the UV region of the light spectrum are shown in Table 1 below.

TABLE 1

Refractive Indices of Fused Silica and Water

| Fused Silica UV Grade (SiO2) | | Water | |
|---|---|---|---|
| Wavelength (nm) | Refractive Index | Wavelength (nm) | Refractive Index |
| 170 | 1.615 | 172 | 1.568 |
| 185 | 1.575 | 185 | 1.549 |
| 200 | 1.550 | 200 | 1.543 |
| 214 | 1.534 | 215 | 1.513 |
| 280 | 1.494 | 280 | 1.492 |
| 302 | 1.487 | 305 | 1.475 |
| 436 | 1.467 | 450 | 1.344 |
| 546 | 1.460 | 550 | 1.336 |
| 656 | 1.456 | 650 | 1.331 |

As shown in Table 1, water has about the same refractive index as UV grade fused silica glass in the ultraviolet (UV) portion of the light spectrum.

Ultraviolet (UV) radiation is transmitted from the high intensity ultraviolet lamp 40, passes through the ultraviolet inlet aperture 35, and enters the lower ultraviolet window surface 36 as shown in FIG. 2. It is desirable to minimize the distance between lamp 40 and aperture 35 to preclude UV absorption by fluid-borne or surface contaminants. In certain embodiments, aperture 35 is fashioned with one or more lens elements (to enhance the optical coupling efficiency. A first UV light ray 71 exits lower ultraviolet window surface, is bent by refraction, and enters the fluid 5, defining a second UV light ray 72. The second UV light ray 72 impinges upon the internal surface 13 of the fluid inlet tube 10, which is in contact with the fluid 5, at an incidence angle 1, where incidence angle 1 is measured with reference to the surface normal of internal surface 13. As the second UV light ray 72 enters a sidewall of the fluid inlet tube 10, it is bent by refraction and redirected at a new internal reflection angle 2, defining a third UV light ray 73.

The value of angle 2, as defined by Snell's Law, is a function of incident angle 1 and the refractive indices of the fluid 5 and the material, such as UV-grade silica, from which the fluid inlet tube 10 is constructed. The third UV light ray 73 continues through the fluid inlet tube 10 material and impinges upon the external surface 14 of the fluid inlet tube that is in contact with the concentric gap 15. The third UV light ray 73 is reflected back into the sidewall of the fluid inlet tube 10, defining a fourth UV light ray 74 when the refractive indices of the fluid inlet tube 10 material and the concentric gap 15 meet total internal reflection conditions as defined by Snell's Law. The refractive index of the concentric gap 15 is defined by the material contained in the concentric gap or by the refractive index of a vacuum if no material is contained within the concentric gap 15.

It is a feature of my invention that a light pipe 100 region, as defined by an initial optical trajectory from UV light source 40, exists for at least part of the length of the fluid inlet tube 10. Therefore, it is required that the incidence angle 2 be limited to a predetermined range in accordance with the refractive indices of the fluid 5, the material from which the fluid inlet tube 10 is constructed, and the concentric gap 15. In a preferred embodiment of my invention, the fluid inlet tube 10 is constructed from UV-grade silica glass, the fluid 5 to be disinfected is water, and the concentric gap 15 contains dry air.

Figure 4:
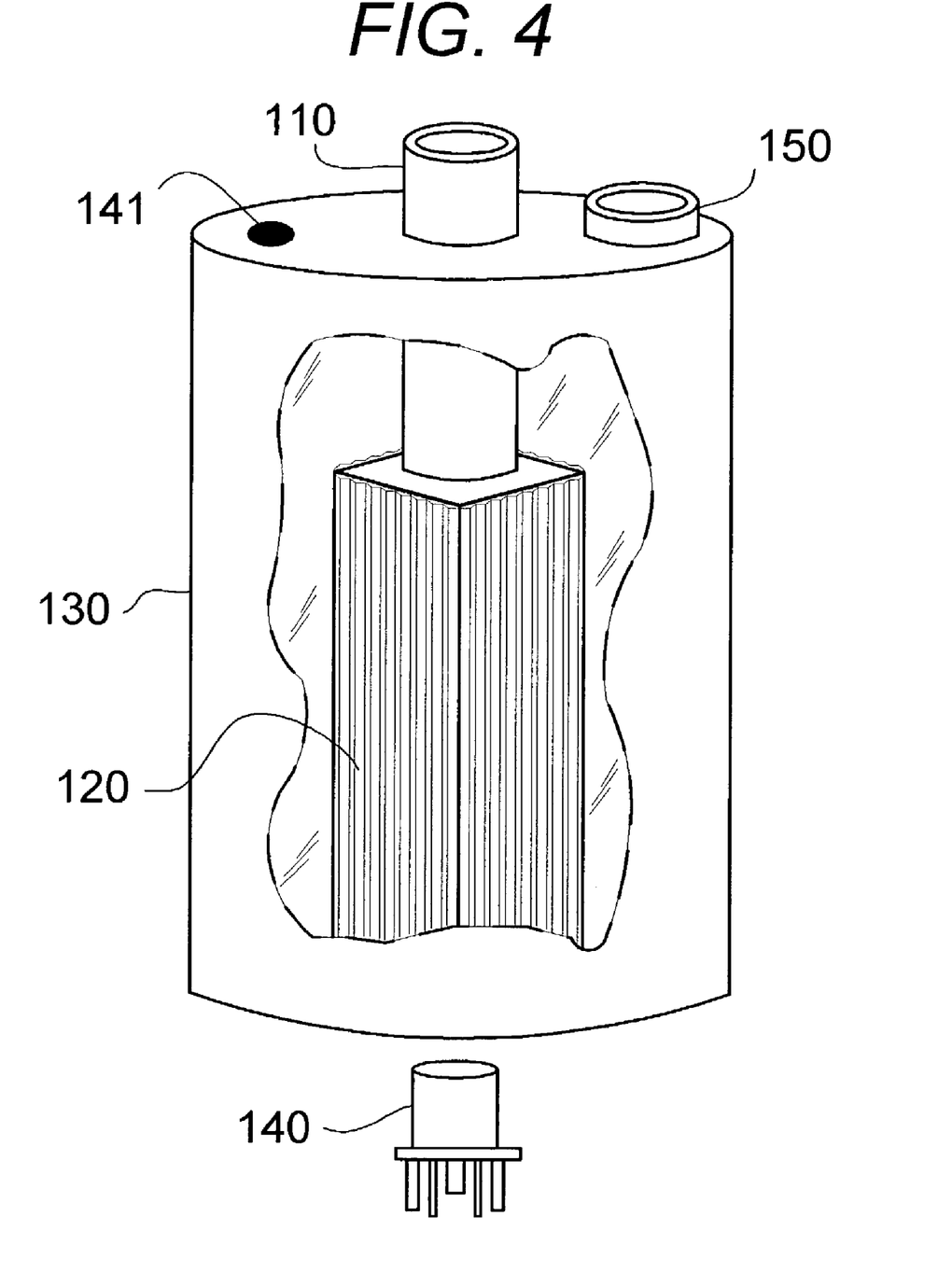
FIG. 4 depicts an apparatus for disinfecting air using ultraviolet radiation (UV) in accordance with one illustrative embodiment of my invention.
Figure 5:
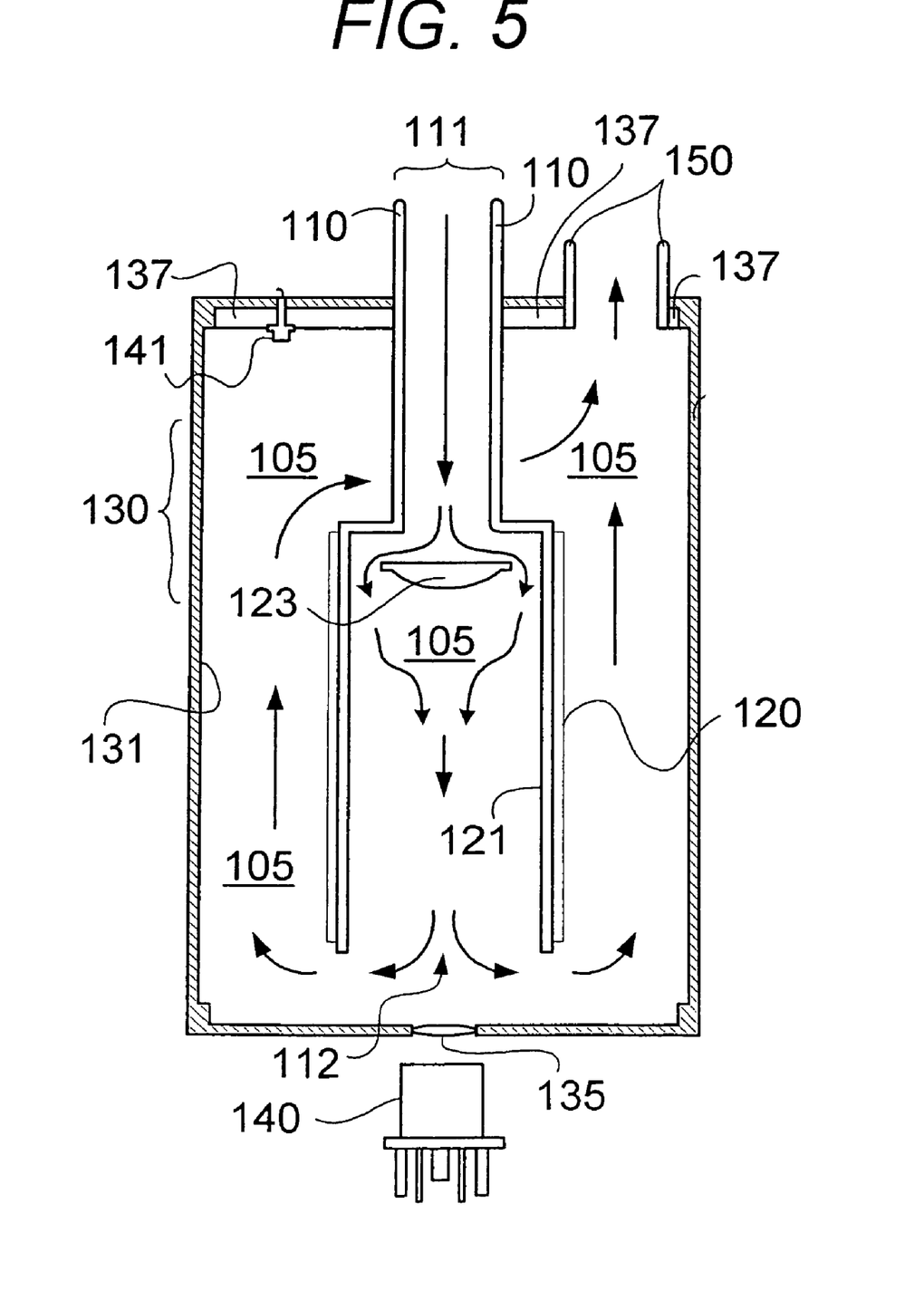
FIG. 5 depicts a sectional view of the UV disinfecting apparatus of FIG. 4.
Figure 6:
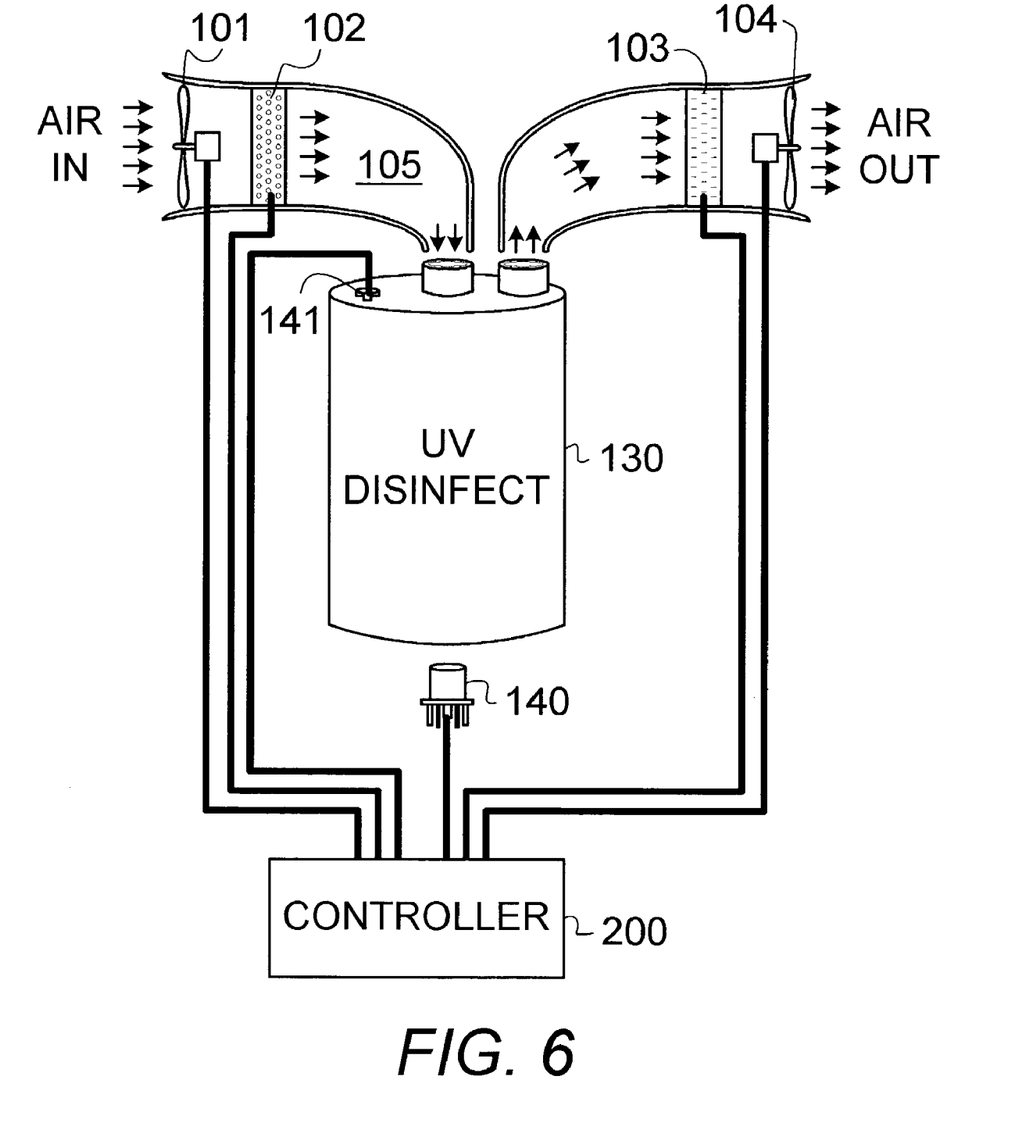
FIG. 6 depicts a block diagram of an air handling system that incorporates my inventive UV disinfecting apparatus.

Another embodiment of my invention suitable for disinfecting air is shown in FIGS. 4-6. Referring first to FIG. 4, an air containment vessel 130 includes an internal surface configured as an ultraviolet mirror 131; for example, the air containment vessel may be constructed from aluminum and the internal surface may be polished aluminum. The air 105 to be disinfected enters the TIR light conduit 110 through an entrance end 111. The light conduit 110 may be manufactured, for example from UV-grade fused silica, especially grades that are highly transmissive in the germicidal wavelengths of 200 nm~300 nm, such as Hereaus Suprasil.

Refer now to FIG. 5, air inlet tube 110 transitions into a section including total internal reflecting (TIR) features 120 that extend from the exit end 110 closest to lamp 140, some distance toward the entrance end 111. This allows some UV light to leak out of air inlet tube 110 and distribute throughout air containment vessel 130. In one embodiment, the TIR features 120 are a plurality of prism light guides, similar to those taught for visible light in Whitehead (U.S. Pat. No. 4,260,220), which describes the solid angle through which TIR can be maintained for an air waveguide. For example, the uncollimated UV energy from a short-arc xenon flash lamp without auxiliary optics can be totally contained via TIR out to a conical half angle of about 27 degrees. UV rays beyond this angle will necessarily leak through the TIR features 120 into the air 105 until it strikes another surface, such as UV mirror 131. Advantageously, air containment vessel 130 maximizes the overall system efficacy by containing the UV, allowing it more opportunity to interact with the air stream. Air containment vessel 130 can also have a square cross section, such as for maximum UV beam homogeneity, or other shape as required.

The air 105 travels through the air inlet tube 110 towards the high intensity UV lamp 140 and exits the light conduit 110 at the exit end 112. The air 105 flow strikes and is diverted around optional deflector mirror 123, which also functions optically to minimize the amount of UV radiation escaping air containment vessel 130.

For embodiments that do not include mirror 123, a portion of UV radiation from the lamp will exit the section of inlet tube 110 having TIR features 120, and enter the upper portion of containment vessel 130. Only that fraction of UV radiation from the lamp that is highly collimated will reach inlet aperture 111. These rays can be further deflected back into containment vessel 130 by introducing, for example, a right angle fitting at the inlet aperture 111.

Continuing to refer to airflow path 105, the air then strikes an ultraviolet (UV) window 135, which forms a portion of the lower end of air containment vessel 130. As discussed earlier, in certain embodiments, window 135 comprises one or more lens elements. The TIR structure, for the embodiments that are primarily designed to disinfect air, have more limited containment angles than the embodiments that are primarily designed to disinfect water. For the embodiments designed to disinfect air, some degree of optical collimation is advantageous, although the principle of etendue requires a larger cross section for the TIR region 120 of tube 110.

Finally, the air 105 flow is redirected to the air outlet 150, which is located in the upper end of the air containment vessel 130. Advantageously, while the air 105 is travelling outside of the TIR section, it receives additional UV irradiation that has been trapped by UV mirror 131, and thus forms a practical embodiment of a high efficiency UV irradation system. Alternatively, the UV exiting the lamp can be collimated with the ~27 degree conical half angle, and injected into a very long TIR guiding structure, thereby achieving extremely high efficacy (i.e. the amount of disinfection per electrical watt).

In a preferred embodiment, a UV sensor 141 is used as a feedback element to ensure that proper irradiance levels are being applied. Apprise Technology (Duluth, Minn.), under the trade name UV Clean, produces a suitable UV sensor that can handle continuous and pulsed UV sources. The UV sensor 141 is located with a view into vessel 130, but without direct view of UV lamp 140. Advantageously, this position enables the sensor to measure the integrated cavity irradiance, and is not prone to variations in the lamp's output distribution. Since the air stream is filtered, cleaning of the sensor's input aperture is minimized. In certain embodiments, such as those where the provision of disinfected air life-critical, redundant UV sources and sensors are employed.

Referring now to FIG. 6, an ultraviolet air disinfecting system that uses my inventive UV disinfecting apparatus, is schematically depicted. Air to be disinfected enters, for example, through inlet fan 101 and passes through air filter 102 to remove contaminants that would degrade the system efficacy by absorbing UV. The filtered air 105 to be disinfected next flows into air containment vessel 30 where it is irradiated by high intensity ultraviolet (UV) lamp 140. After being irradiated, the air flows from the air containment vessel 130, through optional catalytic filter 103, which converts ozone back into breathable oxygen and finally exits through air outlet fan 104. Feedback from sensors are fed into controller 200 which then can regulate the amount of UV introduced into vessel 130, and the flow rate via inlet fan 101 and outlet fan 104. Additionally, for those embodiments that use a pulsed lamp as UV source 40, controller 200 varies the pulse repetition rate. In further embodiments controller 200 can also provide alarm warnings, for example, when sensor 141 detects abnormally low UV irradiation in chamber 130, perhaps signaling the need for the lamp to be replaced.

List of Acronyms Used in the Specification

The following is a list of the acronyms used in the specification in alphabetical order.

| | |
|---|---|
| HEPA | high efficiency particulate air (filter) |
| HVAC | heating, venting, and air conditioning |
| TIR | total internal reflection |
| UV | ultraviolet |

Alternate Embodiments

Alternate embodiments may be devised without departing from the spirit or the scope of the invention. For example, this same system can be adapted for a dual-use application, whereby multiple fluids (e.g. air and water) can be purified.

What is claimed is:

1. A system to disinfect air using ultraviolet radiation (UV), said system comprising:
    (a) an air inlet tube (110) comprising an entrance end (111), a distally opposing exit end (112), an elongate internal surface (121) in contact with said air, and an elongate external surface;
    (b) total internal reflecting features disposed upon at least a portion of at least one of the elongate surfaces of said air inlet tube;
    (c) an air containment vessel (130) disposed around said air inlet tube;
    (d) an ultraviolet inlet window (135) that allows penetration of said air containment vessel by ultraviolet radiation but prevents passage therethrough of air;
    (e) a high intensity ultraviolet lamp (40) providing ultraviolet radiation that passes through said ultraviolet inlet window and impinges upon the internal surface of said air inlet tube; and
    (f) an air outlet (150) extending from said air containment vessel.

2. The system of claim 1 wherein said air inlet tube is constructed from UV-grade silica glass.

3. The system of claim 1 wherein said total internal reflecting features comprise a plurality of prism light guides extending along said external surface of said air inlet tube.

4. The system of claim 1 further comprising a deflector mirror (123) positioned in the path of the air within said air inlet tube.

5. The system of claim 1 wherein said total internal reflecting features are disposed upon at least a portion of a surface of said air inlet tube in a region of said air inlet tube through which the air to be disinfected passes, and
    wherein said ultraviolet radiation impinges on the inner surface of said air inlet tube in said region, said radiation traversing said air inlet tube parallel to said total internal reflecting features disposed upon said surface of said air inlet tube and being guided through said air inlet tube by said total internal reflecting features.

6. An air treatment system for disinfecting air by way of exposure to an ultraviolet light source, the air treatment system comprising:
    an air containment vessel;
    an elongated inlet tube extending into said air containment vessel and having opposite first and second ends, said elongated inlet tube comprising an air inlet at the first end through which air enters into the inlet tube, an internally reflective section and an outlet port at the second end, each of the internally reflective section and the outlet port being substantially contained within said air containment vessel;
    a window disposed through said air containment vessel proximate said outlet port, said window configured to permit ultraviolet light emitted from the light source to impinge upon said internally reflective section and thereby disinfect air flowing through said elongated inlet tube;
    an airflow and light deflector having an airflow deflecting surface facing the air inlet, and further having a light reflective surface facing the window, said airflow and light deflector disposed within said elongated inlet tube proximate said internally reflective section; and
    an air outlet tube coupled to said air containment vessel and configured to permit the flow of disinfected air out of said air containment vessel.

7. An air treatment system according to claim 6 wherein said reflective downstream face faces the ultraviolet light source, and wherein said internally reflective section resides substantially between said reflective downstream face and said window.

8. An air treatment system according to claim 6 wherein said airflow and light deflector is disposed within said internally reflection section such that a substantially annular gap is formed between said airflow and light deflector and said internally reflection section.

9. An air treatment system according to claim 6 wherein said elongated inlet tube comprises:
   a first segment having a first inner diameter; and
   a second segment having a second inner diameter substantially larger than said first inner diameter, said airflow and light deflector residing within said second segment proximate said first segment.

10. An air treatment system according to claim 9 wherein said airflow and light deflector has an outer diameter larger than said first inner diameter, and wherein said airflow and light deflector is positioned so as to substantially prevent ultraviolet light from entering said first segment.

11. An air treatment system according to claim 9 wherein said first segment extends through said air containment vessel, and wherein said second segment comprises:
   a first end coupled to said first segment; and
   a second end including said outlet port, said internally reflective section residing between said first end and said second end.

12. An air treatment system according to claim 11 wherein said airflow and light deflector is disposed within said second segment proximate said first end, and wherein said reflective downstream face comprises a convex deflector mirror.

13. An air treatment system according to claim 6 wherein said internally reflection section, said airflow and light deflector, said outlet port, and said window are substantially co-axial.

14. An air treatment system for disinfecting air with an ultraviolet lamp, comprising:
   an elongate air inlet tube, comprising:
      an inlet section; and
      a UV treatment section fluidly coupled to said inlet section, said UV treatment section having an elongate reflective inner surface and an open end substantially opposite said inlet section;
   a fluid containment vessel containing said UV treatment section and having said inlet section disposed therethrough, an inner surface of said fluid containment vessel cooperating with an outer surface of said UV treatment section to form a chamber fluidly coupled to said open end, said chamber configured to receive treated air from said UV treatment section;
   an outlet port fluidly coupled to said chamber; and
   a window disposed through said fluid containment vessel proximate said open end, said window configured to permit UV light emitted from the ultraviolet lamp to impinge upon said reflective inner surface to disinfect air flowing through said UV treatment section.

15. An air treatment system according to claim 14 wherein the inner diameter of said UV treatment section is substantially larger than the inner diameter of said inlet section.

16. An air treatment system according to claim 14 wherein said fluid containment vessel comprises:
   a first wall having said inlet section and said outlet port disposed therethrough; and
   a second wall substantially opposite said first wall, said second wall having said window disposed therethrough.

17. An air treatment system according to claim 14 wherein an inner surface of said fluid containment vessel is reflective.

18. An air treatment system according to claim 14 wherein said inner surface comprises a plurality of prismatic light guides.

19. An air treatment system according to claim 14 further comprising an airflow and light deflector disposed within said UV treatment section substantially opposite said open end.

20. An air treatment system according to claim 14 further comprising:
   a UV sensor disposed at least partially within said treatment chamber;
   an inlet fan fluidly coupled to said inlet tube; and
   a controller coupled to the ultraviolet lamp, said UV sensor, and said inlet fan, said controller configured to regulate the output of the ultraviolet lamp and the rate of airflow in relation to UV levels within said chamber as related by said UV sensor.

* * * * *